United States Patent
Xiao et al.

(10) Patent No.: US 7,238,823 B2
(45) Date of Patent: Jul. 3, 2007

(54) PLATINUM COMPLEXES WITH MONONITRILE-CONTAINING LIGANDS

(75) Inventors: Zejun Xiao, San Antonio, TX (US); Frederick H. Hausheer, Boerne, TX (US); Pavankumar Petluru, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 11/340,048

(22) Filed: Jan. 26, 2006

(65) Prior Publication Data

US 2007/0004798 A1 Jan. 4, 2007

Related U.S. Application Data

(60) Provisional application No. 60/695,638, filed on Jun. 30, 2005.

(51) Int. Cl.
*C07F 15/00* (2006.01)
*A61K 31/28* (2006.01)

(52) U.S. Cl. .................. 556/137; 546/2; 548/101; 514/359; 514/492

(58) Field of Classification Search ........... 556/137; 546/2; 548/101; 514/359, 492
See application file for complete search history.

(56) References Cited

U.S. PATENT DOCUMENTS

| | | | | |
|---|---|---|---|---|
| 5,107,007 A | * | 4/1992 | Farrell | 556/137 |
| 2002/0165369 A1 | * | 11/2002 | Braman et al. | 536/17.1 |
| 2004/0039051 A1 | * | 2/2004 | Shaw | 514/492 |

OTHER PUBLICATIONS

Kharitonov et al., Doklady Akademii Nauk SSSR, vol. 141, pp. 645-648 (1961).*
Uchiyama, et al., The Isolation, "Characterization, and Isomerization of cis- and trans-Bis(benzonitrile)dichloroplatinum(II)", Bull. Chem. Soc. Jpn., 54:181-85 (1981).

* cited by examiner

*Primary Examiner*—Porfirio Nazario-Gonzalez
(74) *Attorney, Agent, or Firm*—Scott A. Whitaker

(57) ABSTRACT

Disclosed herein are novel platinum-based complexes possessing one nitrile substituent group (mononitrile) covalently-bonded to the platinum, one or more nitrogen donor ligands capable of forming hydrogen bonds with the bases in DNA or RNA and leaving groups (i.e., $L_1$ and $L_2$) which can be hydrolyzed in vivo to active species, which can then form coordinate adducts with DNA or RNA at the Guanine or Adenine bases thereof. Also disclosed herein are the reaction schemes for the synthesis of said platinum complexes, as well as methods of treatment of various types of cancer by the administration of a pharmaceutically-effective dose of said novel platinum complexes.

65 Claims, No Drawings

PLATINUM COMPLEXES WITH MONONITRILE-CONTAINING LIGANDS

RELATED APPLICATIONS

The present application claims priority to Provisional Application Ser. No. 60/695,638, filed Jun. 30, 2005 and entitled: "PLATINUM COMPLEXES WITH MONONITRILE-CONTAINING LIGANDS".

FIELD OF THE INVENTION

The present invention relates to novel platinum complexes possessing mononitrile-containing ligands, pharmaceutically-acceptable salts, and/or derivatives thereof, as well as methods for the synthesis of these aforementioned platinum complexes possessing mononitrile-containing ligands, pharmaceutically-acceptable salts, and/or derivatives thereof. More specifically, the present invention relates to the use of platinum complexes possessing mononitrile-containing ligands, pharmaceutically-acceptable salts, and/or derivatives thereof, for the purpose of inhibiting the growth of cancer cells, pharmaceutically-acceptable formulations of platinum complexes possessing mononitrile-containing ligands and derivatives thereof and methods of administration of platinum complexes possessing mononitrile-containing ligands and derivatives thereof (e.g., dosages, schedules of administration, and routes of administration of said formulations to humans with various forms of cancer).

BACKGROUND OF THE INVENTION

The anti-neoplastic drug cisplatin (cis-diamminedichloroplatinum or "CDDP"), and related platinum based drugs including carboplatin and oxaliplatin, are widely used in the treatment of a variety of malignancies including, but not limited to, cancers of the ovary, lung, colon, bladder, germ cell tumors and head and neck. Platinum complexes are reported to act, in part, by aquation (i.e., to form reactive aqua species), some of which may predominate intracellularly, and subsequently form DNA intra-strand coordination chelation cross-links with purine bases, thereby cross-linking DNA. This mechanism is believed to work predominantly through intra-strand cross-links, and less commonly, through inter-strand cross-links, thereby disrupting the DNA structure and function, which is cytotoxic to cancer cells. Platinum-resistant cancer cells are resilient to the cytotoxic actions of these agents. Certain cancers exhibit intrinsic de novo natural resistance to the killing effects of platinum agents and undergo no apoptosis, necrosis or regression following initial platinum compound treatment. In contrast, other types of cancers exhibit cytotoxic sensitivity to platinum drugs, as evidenced by tumor regression following initial treatment, but subsequently develop an increasing level of platinum resistance, which is manifested as a reduced responsiveness and/or tumor growth following treatment with the platinum drug (i.e., "acquired resistance"). Accordingly, new platinum agents are continually being sought which will effectively kill tumor cells, but that are also insensitive or less susceptible to tumor-mediated drug resistance mechanisms that are observed with other platinum agents.

In attempting to solve this problem, one research group (see, Uchiyama, et al., *Bull. Chem. Soc. Jpn.* 54:181-85 (1981)) has developed cisplatin complexes possessing a nitrile group substituted for each of the amine groups in cisplatin (IUPAC Nomenclature: cis-bisbenzonitriledichloroplatinum(II)). The structural formula for this complex is shown below:

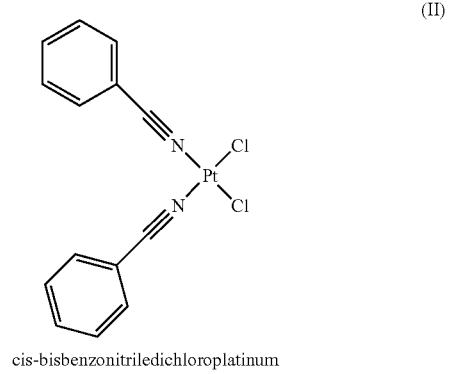

cis-bisbenzonitriledichloroplatinum

In general, nitrile-ligand based platinum complexes are less polar and more lipophilic (i.e., hydrophobic) than the currently-marketed platinum-based drugs, and thus can be dissolved into less polar solvents including, but not limited to, methylene dichloride, chloroform, acetone, N,N-dimethylformide, N,N-dimethylacetamide, and the like. This greater lipophilicity may allow such complexes to be taken up more readily by cancer cells, by facile diffusion/transport through the lipid bilayer of the cell membrane, than similar, currently utilized chemotherapeutic agents. The greater lipophilicity may, therefore, increase the available concentration of the platinum species that can participate in cytotoxic anti-tumor effects on the DNA within cancer cells.

Additionally, the lone pair of electrons on nitrogen in the nitrile group is located in the sp hybrid orbital, which is closer to the nitrogen nucleus than the $sp^3$ hybrid orbital in the amine ligand. Thus, in platinum complexes, the attraction of the nitrogen nucleus in nitrile ligand for the lone pair of sharing electrons with platinum is greater than in the ammine ligand. This effect results in decreasing the ionic effect between platinum (II) and the leaving group, and increasing their covalent bonding characteristics. As a result, the leaving groups are more difficulty to displace by substitution, including aquation, and therefore slower rates of aquation are observed in nitrile N-donor platinum complexes as compared to ammine platinum complexes. It appears that both the nitrile ligand-based platinum complexes and the intermediate platinum complexes they form upon hydrolysis, possess a slower rate of reaction with naked DNA compared to ammine ligand-based platinum complexes. It is assumed that the slower rate of cross-linkage formation of platinum complexes with DNA bases may be less susceptible to tumor-mediated platinum-DNA repair mechanisms, which is one of the key platinum drug resistance mechanisms. In addition, and equally important from a pharmacological, toxicological, chemical and drug-resistance circumvention mechanistic point of view, the nitrile-, azido-, and R—N═N-containing platinum complexes described below are predicted to be substantially less chemically reactive than, e.g., cisplatin, carboplatin and oxaliplatin. Therefore, these nitrile-, azido-, and R—N═N-containing platinum complexes react substantially more slowly with, and thereby avoid unwanted platinum-sulfur and platinum-nitrogen conjugates with, the thiols, disulfides, and proteins/peptides present in vivo; specifically the sulfur-containing physiological thiols, disulfides, and peptides/ amino acids, including but not limited to, glutathione, cysteine, homocysteine, methionine, and all other sulfur-containing and imidazole-containing (e.g., histidine), or arginine or lysine di- tri- and larger peptides, that participate in tumor-mediated platinum drug resistance. Therefore, these novel nitrile, azido, and other nitrogen ligand-based platinum complexes have potential to circumvent de novo and acquired tumor-mediated cisplatin resistance and kill cancer cells that possess both natural and acquired resistance to other known platinum drugs. The platinum complexes described below are also thought to permit controlled reduction of the chemical reactivity of the platinum species to such a degree that greater amounts of the platinum species are also delivered intracellularly with their original chemical entities. This improved delivery of platinum that is available for intracellular DNA adduct formation is mediated by a substantial reduction in the amount of non-effective and non-specific reactions of these novel platinum species with proteins and physiological thiols and disulfides, which can prevent or attenuate the antitumor effects of conventional platinum complexes.

The reaction for cisplatin hydrolysis is illustrated below in Scheme I:

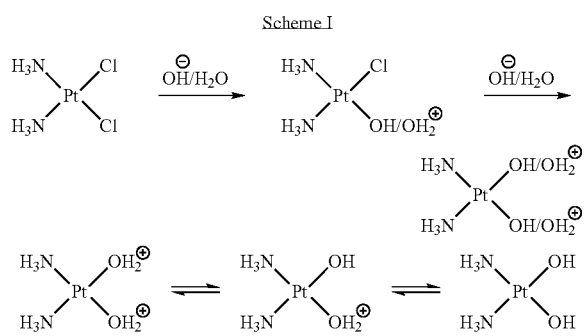

In neutral pH (i.e., pH 7), deionized water, cisplatin hydrolyze to monoaqua/monohydroxy platinum complexes, which is less likely to further hydrolyze to diaqua complexes. However, cisplatin can readily form monoaqua and diaqua complexes by precipitation of chloro ligand with inorganic salts (e.g., silver nitrate, and the like). Also, the chloro ligands can be replaced by existing nucleophile (e.g., nitrogen and sulfur electron donors, etc.) without undergoing aquation intermediates.

Cisplatin is relatively stable in human plasma, where a high concentration of chloride prevents aquation of cisplatin. However, once cisplatin enters a tumor cell, where a much lower concentration of chloride exists, one or both of the chloro ligands of cisplatin is displaced by water to form an aqua-active intermediate form (as shown above), which in turn can react rapidly with DNA purines (i.e., Adenine and Guanine) to form stable platinum—purine—DNA adducts. One limitation associated with these bis-nitrile platinum complexes is that their DNA adducts may not be as stable as cisplatin-DNA adducts, because the ammine groups in cisplatin participate in local hydrogen bonding with the DNA structure to stabilize these DNA-platinum complexes. The lack of local hydrogen bonding interaction between the bis-nitrile platinum complexes and the DNA structure potentially decreases the binding affinity of bis-nitrile platinum complexes with DNA. Therefore, their adducts with DNA bases may be more susceptible to tumor-mediated platinum-DNA repair mechanisms. Thus, there remains a need for new, novel platinum complexes that can form more stable complexes with DNA bases (with increased binding affinity) and be readily taken up by tumor cells. These complexes may be markedly more effective against chemotherapy-resistant tumors than either cisplatin or the currently-available chemotherapeutic agents.

BRIEF SUMMARY OF THE INVENTION

Disclosed herein are novel platinum-based complexes possessing one nitrile substituent group covalently-bonded to the platinum, one or more nitrogen donor ligands capable of forming hydrogen bonds with the bases in DNA or RNA and leaving groups (i.e., $L_1$ and $L_2$) which can be hydrolyzed in vitro and in vivo to active species, which can then form coordinate complexes with DNA or RNA at the Guanine or Adenine bases thereof. The reaction scheme for hydrolysis of the leaving groups in these novel platinum-based complexes disclosed herein would be analogous to that shown above for cisplatin, where the intermediates at the leaving group sites include $OH/OH_2^+$; $OH_2^+$; and OH. Additionally disclosed herein are novel platinum-based complexes possessing azido, substituted azido (e.g., R—N=N=N—), and R—N=N— groups at R and $R_1$ in a cis configuration on the platinum atom with numerous $L_1$ and $L_2$ (leaving group) substitutions which are also capable of hydrogen or electrostatic bonding with DNA.

Unlike bis-nitrile platinum complexes, mononitrile platinum complexes retain the ammine donor ligand, and thus also provide a strong hydrogen bonding capability in the area close to the platinum nucleus. Hydrogen bonding between platinum moieties and DNA bases may increase their binding affinity and stabilizes the resulting adducts. Accordingly, this stabilizing effect may serve to reduce or even eliminate tumor-mediated platinum-DNA repairs and increase therapeutic index. These platinum complexes are also thought to be more easily transported into tumor cells and enhance uptake of drugs by cisplatin resistant tumor cells, due to the increased lipophilicity of nitrile functional group.

These novel complexes are likely to be useful as antineoplastic agents, and in modulating or interfering with the synthesis of DNA or RNA in vitro or in vivo, as they are capable of forming a platinum coordinate complex with an intact or nascent DNA or RNA, and thereby interfere with or actually stop synthesis, transcription, or replication.

The novel platinum-based complexes disclosed herein include, but are not limited to, structures wherein, either one or both of $L_1$ and $L_2$ are leaving groups, which are hydrolyzed in the intracellular environment to generate a first hydroxyl groups at the leaving group positions and then be protonated to produce water, leaving the molecule labile to nucleophilic substitution which can be directly replaced by nucleophilic reagents under intracellular conditions (e.g., Guanine-N7). Thus, through reaction with the Guanine or Adenine base of a DNA (or possibly also an RNA) oligonucleotide, at the 7 position thereof, platinum is capable of rapidly undergoing chelation with said oligonucleotide and cross-linking it with other oligonucleotides, so as to inhibit or prevent further oligonucleotide chain extension. Generally, $L_1$ and $L_2$ should both be leaving groups, but the complexes described herein are often capable of forming complexes with nucleic acids, even if only one of $L_1$ and $L_2$ is a leaving group.

DETAILED DESCRIPTION OF THE INVENTION

The preferred embodiments herein described are not intended to be exhaustive, or to limit the invention to the precise forms disclosed. They are chosen and described to best illustrate the principles of the invention, and its application and practical use to best enable others skilled in the art to follow its teachings.

DEFINITIONS

All definitions provided by: *Hawley's Condensed Chemical Dictionary*, 14$^{th}$ Edition, John Wiley & Sons, Inc., Publishers ((2001) and *American Hospital Formulary Service, Drug Information*, American Society of Health-System Pharmacists, Publishers (1999).

"Scaffold" means the fixed structural part of the molecule of the formula given.

"Nucleophile" means an ion or molecule that donates a pair of electrons to an atomic nucleus to form a covalent bond; the nucleus that accepts the electrons is called an electrophile. This occurs, for example, in the formation of acids and bases according to the Lewis concept, as well as in covalent carbon bonding in organic compounds.

"Pharmaceutically-acceptable salt" means salt derivatives of drugs which are accepted as safe for human administration. In the present invention, mononitrile platinum complexes may comprise various salts, including but not limited to: inorganic salts (e.g., silver nitrate, silver sulfate) and alkaline earth metal salts.

"Fragments", "Moieties" or "Substituent Groups" are the variable parts of the molecule, designated in the formula by variable symbols, such as $R_x$, X or other symbols. Substituent Groups may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y"—$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond(alkenyl) or triple bond (alkynyl) between two of the carbon atoms;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic complexes of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contain from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Azide" means any group of complexes having the characteristic formula $R(N_3)x$. R may be almost any metal atom, a hydrogen atom, a halogen atom, the ammonium radical, a complex $[CO(NH_3)_6]$, $[Hg(CN)_2M]$, (with M=Cu, Zn, Co, Ni) an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing complexes possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Substituted" modifies the identified fragments (moieties) by replacing any, some or all of the hydrogen atoms with a moiety (moieties) as identified in the specification. Substitutions for hydrogen atoms to form substituted complexes include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

As used herein "chemotherapeutic agent" or "chemotherapy agent" or "antineoplastic agent" refer to an agent that reduces, prevents, mitigates, limits, and/or delays the growth or metastases of neoplasms, or kills neoplastic cells directly by necrosis or apoptosis of neoplasms or any other mechanism. Chemotherapeutic agents include, for example, fluropyrimidine; pyrimidine nucleosides; purine nucleosides; anti-folates, platinum complexes; anthracycline/anthracenedione; epipodopodophyllotoxin; camptothecin; hormones; hormonal complexes; antihormonals; enzymes, proteins, and antibodies; vinca alkaloids; taxanes; antimirotubule agents; alkylating agents; antimetabolites; topoisomerase inhibitors; antivirals; and miscellaneous cytotoxic and cytostatic agents. "Chemotherapy" refers to treatments using chemotherapeutic agents, chemotherapy agents, or antineoplastic agents.

As used herein, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; and/or an increase in duration of chemotherapeutic therapy.

As used herein, the term "reducing" includes reducing, preventing, mitigating, delaying the onset of, attenuating the severity of, and/or hastening the resolution of a neoplasm or cancer in a subject, including preventing the further development of, or the development of more severe forms of said neoplasm or cancer, in whole or in part, or ameliorating or controlling such neoplasm or cancer in said the subject.

As used herein "adverse symptom" or "adverse side-effect" means a manifestation or condition that is reported by the patient (e.g., nausea, chills, depression, numbness, tingling, anorexia, dysguesia, and the like); whereas an "adverse sign" means an objective finding that is a physically observable manifestation of a condition, adverse event or disease in the patient (e.g., palpable purpura, maculopapular rash, spider angioma, Chvostek's sign, Babinski's sign, Trousseau's sign, opisthotonos, and the like).

Disclosed herein are novel platinum-based complexes possessing: (i) a single (i.e., mono) nitrile substituent group covalently-bonded to the platinum; (ii) one or more nitrogen donor ligands capable of forming hydrogen bonds with the bases in DNA or RNA and (iii) leaving groups which can be hydrolyzed in vivo to produce active species, which can then form coordinate complexes with DNA or RNA at the Guanine or Adenine bases thereof. The reaction scheme for hydrolysis of the leaving groups in these novel platinum-based complexes disclosed herein would be analogous to that shown above for cisplatin, where the intermediates at the leaving group sites include $OH/OH_2^+$; $OH_2^+$; and $OH$.

Additionally disclosed herein are novel platinum-based complexes possessing azido, substituted azido (e.g., R—N=N=N—) and R—N=N— groups at R and $R_1$ in a cis configuration on the platinum atom with $L_1$ and $L_2$ (leaving group) substitutions which may include, but are not limited to, carboxylate, alkoxyl, hydroxyl, water, peroxide, sulfur, disulfide, sulfoxide, chloride, bromide, fluoride, iodide, amine, pyridine, pyrrole, chlorate, nitrate, nitrite, sulfate, sulfite and phosphate, as well as novel derivatives thereof. R substitutions may include, but are not limited to, alkyl, heterocycles, and the like. It should also be noted that these aforementioned platinum-based complexes are also novel, and would be capable of hydrogen or electrostatic bonding with DNA.

Unlike bis-nitrile platinum complexes, mononitrile platinum complexes retain the ammine donor ligand, and thus also provide a strong hydrogen bonding capability in the area close to the platinum nucleus. Hydrogen bonding between platinum moieties and DNA increases their binding affinity and stabilizes the resulting adducts. These platinum complexes are also thought to be more easily transported into tumor cells, due to the increased lipophilicity of nitrile functional group.

These novel complexes are likely to be useful as antineoplastic agents, and in modulating or interfering with the synthesis of DNA or RNA in vitro or in vivo, as they are capable of forming a platinum coordinate complex with an intact or nascent DNA or RNA and thereby interfering with or stopping synthesis, transcription or replication.

The novel platinum-based complexes disclosed herein include, but are not limited to, the following structural formulas (e.g., Formula A, B and C):

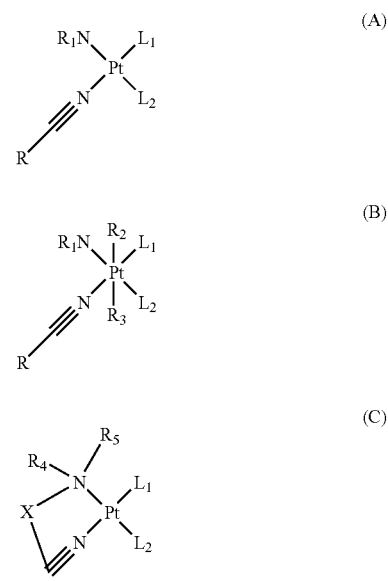

wherein, either one or both of $L_1$ and $L_2$ are leaving groups, which are hydrolyzed in the intracellular environment to generate: (i) first hydroxyl groups at the leaving group positions and (ii) then produce water, leaving the molecule labile and suitable for nucleophilic substitution. Thus, through reaction with the Guanine or Adenine base of a DNA (or possibly also an RNA) oligonucleotide, at the 7 position thereof, platinum is capable of rapidly chelating with it and cross-linking it with other oligonucleotides to inhibit or prevent further oligonucleotide chain extension.

Examples of suitable $L_1$ and $L_2$ moieties include, but are not limited to, carboxylate, alkoxyl, hydroxyl, water, peroxide, sulfur, disulfide, sulfoxide, chloride, bromide, fluoride, iodide, amine, pyridine, pyrrole, chlorate, nitrate, nitrite, sulfate, sulfite and phosphate. Generally, $L_1$ and $L_2$ should both be leaving groups, but the complexes described herein are often capable of forming complexes with nucleic acids, even if only one of $L_1$ and $L_2$ is a leaving group.

The N groups with the $R_1$, $R_4$, $R_5$ in the complexes disclosed above are typically carrier ligands, which include, but are not limited to, primary, secondary or tertiary amine groups; pyridine, pyrrole, pyrazole, or imidazole (wherein $R_1$, $R_4$, $R_5$ are hydrogen, alkyl, cycloalkyl, aryl, acetate, or:

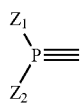

wherein, $Z_1$ and $Z_2$ are the same or different, and are functional groups including O, N, S, $NH_2$, Sulfonyl, or Sulfoxide.

The carrier ligands should be neutral in charge within said complex, and the carrier ligands and the R group (e.g., alkyl, cycloalkyl, aryl or acetate, or another suitable functional group) should not be so large as to cause steric interfere with DNA chelation. As noted above, amine groups in the carrier ligand position can generate hydrogen bonding which can help stabilize the DNA adducts.

The X in Formula C, set forth above in the present invention, is an alkyl chain defined as comprising a straight or branched chain hydrocarbon of between 1 and 20 atoms, which can be saturated or unsaturated, and may include heteroatoms such as nitrogen, sulfur, and oxygen.

$R_2$ and $R_3$ are the same or different groups and include, but are not limited to, F, Cl, Br, I, N, S, or $OR_6$ (where $OR_6$ is carboxylate, alkoxyl, hydroxyl, or water, etc).

As previously discussed, in the present application, the term "alkyl" is defined as comprising a straight or branched chain hydrocarbon of between 1 and 20 atoms, which can be saturated or unsaturated, and may include heteroatoms such as nitrogen, sulfur, and oxygen. The term "alkylene" is defined as comprising a bridging hydrocarbon having from 1 to 6 total carbon atoms which is bonded at its terminal carbons to two other atoms ($-CH_2-$)$_x$ where x is 1 to 6. The term "aryl" is defined as comprising as an aromatic ring system, either fused or unfused, preferably from one to three total rings, with the ring elements consisting entirely of 5-8 carbon atoms.

Scheme II, below, illustrates the novel mononitrile-based platinum complexes disclosed herein forming a coordinate adduct with a DNA base:

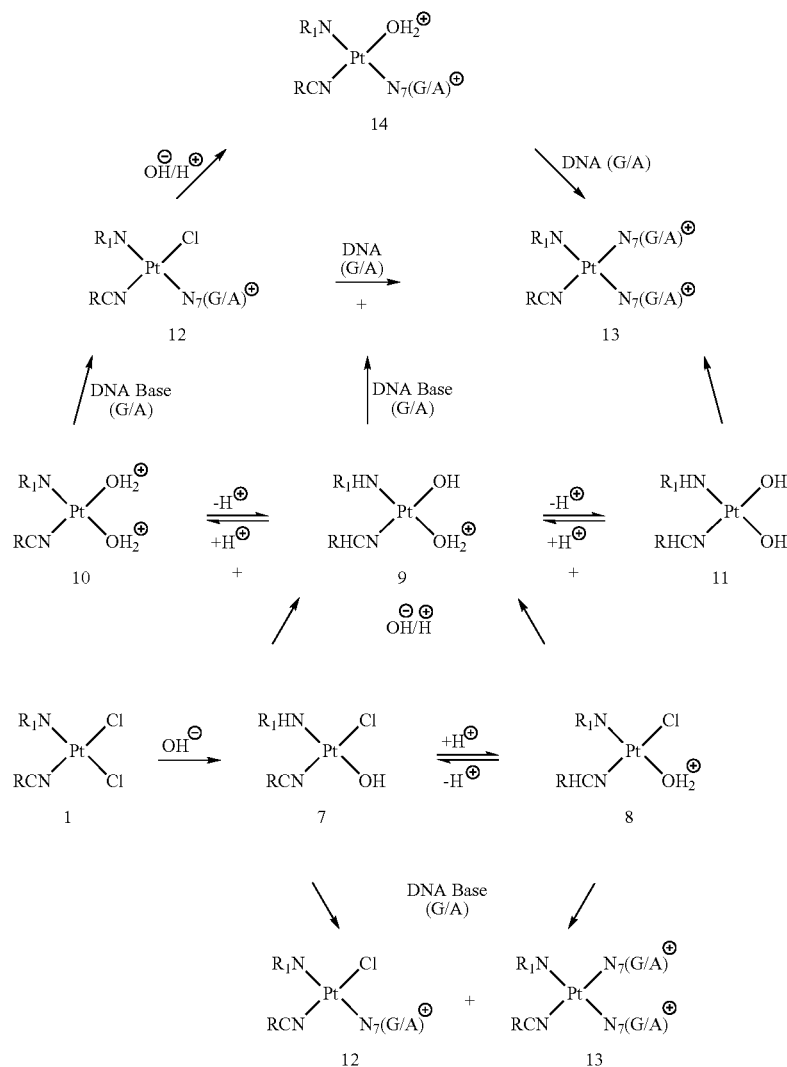

As may be ascertained from Scheme II, above, the asymmetric nature of one ammine ligand and one nitrile ligand in these complexes (1) causes differing rates of hydrolysis at the leaving groups to be expected. Referring to this aforementioned reaction scheme, presumably a nucleophilic hydroxyl group initially substitutes for chloro at the trans-position of the ammine ligand to form the monohydroxy species (7), which is further protonated to form the monoaqua species (8). Both monohydroxy and monoaqua intermediates readily react with the DNA base (i.e., Guanine or Adenine) to form DNA adducts (12, 13). The adduct (12) can then either further hydrolyze to the monoaqua species (14) to form the adduct (13), or directly react with the DNA base to form the adduct (13). Monohydroxy (7) and monoaqua (8) can also further hydrolyze to the monohydroxy-monoaqua species (9), diaqua species (10), and dihydroxy species (11). Under physiological conditions, the platinum monohydroxy species (7) is predominately present, and both the diaqua (10) and dihydroxy (11) species are present only at very low concentration.

Methods I and II, as set forth below, are two general methods of synthesis that can be employed in making the novel platinum-based complexes, including nitrile functional groups, as disclosed in the present invention. Methods I and II are illustrative of the basic methods of synthesis, followed by a more detailed description of the actual experimental reaction conditions and reactants, utilized. It should be noted, however, that the synthesis procedures relating to Method II were not actually performed, but are fully expected to yield the desired products by following the synthetic experimental methodologies described below.

Method I

A detailed procedure for the preparation of a variety of mononitrile-containing platinum complexes are described in Scheme III and Scheme IV. Treatment of substituted-ammine halogen platinum complexes with tetra-alkylamonium halogen salts (e.g., tetraethylammonium chloride) in a polar solvent (e.g., N,N-dimethylacetamide) at heated reaction conditions produces amminetrichloroplatinate, which is then further reacted with alkali or alkaline earth metal salts to give rise to the corresponding platinate salts.

The subsequent reaction of the above salts with alkyl or aryl nitriles under a variety of reaction conditions furnishes novel mononitrile containing platinum complexes (1). Treatment of mononitrile complexes with inorganic salts (e.g., silver nitrate, silver sulfate, and the like) produces the corresponding monoaqua or diaqua platinum complexes (3), depending upon the stochimetric amount of reagents used. Platinum complexes (2) can be obtained through addition of alkali or alkaline earth metal bromides/iodides, which can be further transformed to the monoaqua and diaqua complexes. The reactive monoaqua and diaqua intermediates can be used for the synthesis of a variety of mononitrile platinum complexes (4) with $L_1$ and $L_2$ as leaving groups. Oxidation of complexes (4) with oxidative reagents (e.g., hydrogen peroxide) gives axial ligand ($R_2$ and $R_3$) containing mononitrile platinum (IV) complexes (5). All platinum complexes above are predicted to have chemotherapeutic and antineoplastic effects.

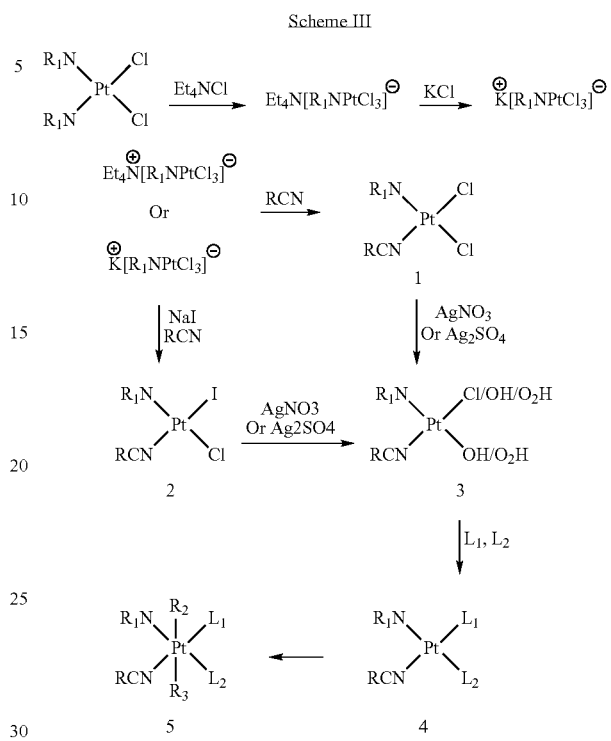

Scheme III

Wherein, $L_1$, $L_2$ are the same or different, and include, but are not limited to, carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphine, thio phosphonate, alkyl phosphoramidates, and phosphoramidates.

The first two reactions shown in Method I were performed as described in an article by Cai, L., et al., J. Med. Chem. 44:2959-2965 (2001). Utilizing these two reactions as starting material, the remaining reactions in Method I were designed and performed.

In the reactions shown below, potassium tetrachloroplatinate and cisplatin (cis-diamminedichloroplatinum) were purchased from Sigma-Aldrich Co. High Resolution Mass Spectrometry (HRMS) of all complexes was measured by the mass spectroscopy laboratory at Ohio State University. The $^1$H NMR and $^{195}$Pt Nuclear Magnetic Resonance (NMR) spectra were obtained on a Varian 300 spectrometer at BioNumerik Pharmaceuticals, Inc.

Method II

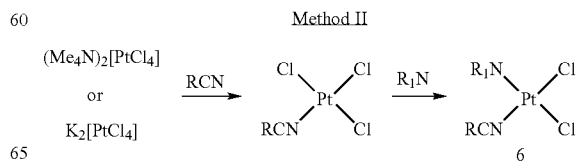

SPECIFIC EXAMPLES OF SYNTHESIS OF PLATINUM COMPLEXES

I. Preparation of $Et_4N[PtCl_3(NH_3)]$ tetraethylammounium amminetrichloroplatinate; $K[PtCl_3(NH_3)]$ potassium amminetrichloroplatinate A mixture of cisplatin (8.1 g) and tetraethylammonium chloride (5.64 g) in 300 mL of N,N-dimethylacetamide was heated at 100° C. with bubbling of argon for 7 hours. The resulting dark orange solution was concentrated to a final volume of approximately 50 mL. To this mixture was added a solution of hexane and ethyl acetate (400 mL; 1:1 v/v). The resulting suspension was put in refrigerator (−5° C.) for 14 hours. The light pale yellow solution was then decanted and the orange oil was extracted with 100 mL of deionized water. The yellow precipitate was filtered, and the filtrate was lyophilized to give a yellow solid of pure tetraethylammounium amminetrichloroplatinate. The above platinate was dissolved in 100 mL of deionized water, and acid exchange resin was added. The mixture was stirred for 30 min. and the resin was filtered. The filtrate was concentrated to 10 mL, and 10 mL of saturated KCl solution was added. The resultant solution was put in a refrigerator at 2° C. for 16 hours to give the desired product of potassium amminetrichloroplatinate (orange solid, 2.62 g; 41%).

$^{195}$Pt NMR δ-1880 ppm. Predicted HRMS for $K_2PtNH_3Cl_3$: 394.824736; found: 394.824202.

II. Preparation of cis-amminebenzonitriledichloroplatinum (II); $C_7H_8Cl_2N_2Pt$; $PtCl_2(NH_3)(C_6H_5CN)$ To a solution of $K[PtNH_3Cl_3]$ (150 mg) in 4 mL of deionized water was added 0.2 mL of benzonitrile. The resulting mixture was heated and stirred for 12 hours. The pale yellow precipitate was filtered, washed with deionized water and ethyl ether, and dried under high vacuum to give a crude product. Recrystallization from tetrahydrofuran and acetone afforded a pure product (pale yellow solid, 25 mg; 17%).

$^1$H NMR in acetone-$d_6$: δ: 7.89(m, 2H), 7.80 (m, 1H), 7.63 (m, 2H), 4.08 (br, $^3$H). $^{195}$Pt NMR δ-2244 ppm. Predicted HRMS for $C_7H_8Cl_2N_2PtNa^+$: 407.9604361 amu; found: 407.96028 amu.

III. Preparation of cis-amminedichloro(3-methoxybenzonitrile)platinum(II); $C_8H_{10}Cl_2N_2OPt$; $PtCl_2(NH_3)(3-CH_3OC_6H_4CN)$ To a solution of $K[PtNH_3Cl_3]$ (150 mg) in 3 mL of deionized water was added 65 μL of 3-methoxybenzonitrile. The resulting mixture was heated and stirred for 15 hours. The pale yellow precipitate was filtered, washed with deionized water and ethyl ether, and dried under high vacuum to give a crude product, which was further purified by recrestallization to give the desired pure product (pale yellow solid 25 mg; 17%).

$^1$H NMR in acetone-$d_6$: δ: 7.77 (d, J=8.1 Hz, 1H), 7.51 (m, 2H), 7.37 (m, 1H), 4.10 (br, 3H), 3.93 (s, 3H). $^{195}$Pt NMR δ-2262 ppm. Predicted HRMS for $C_8H_{10}Cl_2N_2OPtNa^+$: 437.971001 amu; found: 437.97080 amu.

IV. Preparation of cis-amminedichloro(3-methoxypropionitrile)platinum(II); $C_4H_{10}Cl_2N_2OPt$; $PtCl_2(NH_3)(3-CH_3OCH_2CH_2CN)$ To a solution of $K[PtNH_3Cl_3]$ (150 mg) in 4 mL of deionized water was added 0.3 mL of 3-methoxypropionitrile. The resulting mixture was heated and stirred for 24 hours. The pale yellow precipitate was filtered, washed with deionized water and ethyl ether, and dried under high vacuum to give a crude product. Recrystallization from tetrahydrofuran and acetone afforded a pure product (pale yellow solid, 38 mg; 29%).

$^1$H NMR in acetone-$d_6$: δ: 3.25 (t, 2H), 3.68 (t, 2H), 3.94 (br, 3H). $^{195}$Pt NMR δ-2248 ppm. Predicted HRMS for $C_4H_{10}Cl_2N_2OPtNa^+$: 389.97100 amu; found: 389.97047 amu.

V. Preparation of cis-amminedichloro(3-ethoxybenzonitrile)platinum(II); $C_9H_{12}Cl_2N_2OPt$; $PtCl_2(NH_3)(3-EtOC_6H_5CN)$ To a solution of $K[PtNH_3Cl_3]$ (150 mg) in 5 mL of deionized water was added 0.2 mL of 3-ethoxybenzonitrile. The resulting mixture was heated and stirred for 24 hours. The pale yellow precipitate was filtered, washed with deionized water and ethyl ether, and dried under high vacuum to give a crude product. Recrystallization from tetrahydrofuran and acetone afforded a pure product (pale yellow solid; 12 mg).

$^1$H NMR in DMF-$d_7$: δ: 7.96 (m, 1H), 7.52 (m, 2H), 7.38 (m, 1H), 4.62 (br, 3H), 4.15 (q, 2H), 1.32 (t, 3H). $^{195}$Pt NMR δ-2250 ppm. Predicted HRMS for $C_9H_{12}Cl_2N_2OPtNa^+$: 451.986667 amu; found: 451.98697 amu.

VI. Preparation of cis-amminecyclohexanecarbonitriledichloroplatinum(II); $C_7H_{14}Cl_2N_2Pt$; $PtCl_2(NH_3)(C_6H_{11}CN)$ To a solution of $K[PtNH_3Cl_3]$ (150 mg) in 4 mL of deionized water was added 0.1 mL of cyclohexanecarbonitrile. The resulting mixture was heated and stirred for 12 hours. The pale yellow precipitate was filtered, washed with deionized water and ethyl ether, and dried under high vacuum to give a crude product. Recrystallization from tetrahydrofuran and acetone afforded a pure product (pale yellow solid, 50 mg; 35%).

$^1$H NMR in DMF-$d_7$: δ: 4.57 (br, 3H), 3.36 (m, 1H), 1.88 (m, 2H), 1.70 (m, 3H), 1.46 (m, 3H), $^{195}$Pt NMR δ-2244 ppm. Predicted HRMS for $C_7H_{14}Cl_2N_2PtNa^+$: 414.007386 amu; found: 414.00786 amu.

VII. Preparation of cis-amminecyclopropylcyanidedichloroplatinum(II); $C_4H_8Cl_2N_2Pt$; $PtCl_2(NH_3)(C_3H_5CN))$ To a solution of $K[PtNH_3Cl_3]$ (150 mg) in 4 mL of deionized water was added 0.4 mL of cyclopropylcyanide. The resulting mixture was heated and stirred for 24 hours. The pale yellow precipitate was filtered, washed with deionized water and ethyl ether, and dried under high vacuum to give a yellow product. Recrystallization from tetrahydrofuran and acetone afforded the desired pure product.

$^1$H NMR in aceton-$d_6$: δ: 3.87 (br, 3H), 1.93 (m, 1H), 1.20 (m, 4H), $^{195}$Pt NMR δ-2238 ppm. . Predicted HRMS for $C_4H_8Cl_2N_2PtNa^+$: 371.960436 amu; found: 371.96202 amu.

VIII. Preparation of cis-amminedichloro(3-furonitrile)platinum(II); $C_4H_3Cl_2N_2OPt$; $PtCl_2(NH_3)(C_4H_3OCN)$ To a solution of $K[PtNH_3Cl_3]$ (150 mg) in 5 mL of deionized water was added 3-furonitrile (47 mg). The resulting mixture was heated and stirred for 36 hours. The pale yellow precipitate was filtered, washed with deionized water and ethyl ether, and dried under high vacuum to give a yellow product. Recrystallization from tetrahydrofuran and acetone afforded the desired pure product.

$^1$H NMR in aceton-$d_6$: δ: 8.61 (m, 1H), 7.85 (m, 1H), 6.96 (m, 1H), 4.05 (br, 3H). $^{195}$Pt NMR δ-2239 ppm. . Predicted HRMS for $C_4H_8Cl_2N_2PtNa^+$: 397.939701 amu; found: 397.93959 amu.

IX. Preparation of cis-amminedichloro(2-methoxybenzonitrile)platinum(II); $C_8H_{10}Cl_2N_2OPt$; $PtCl_2(NH_3)(2-CH_3OC_6H_4CN)$ To a solution of $K[PtNH_3Cl_3]$ (150 mg) in 4 mL of deionized water was added 0.3 mL of 2-methoxybenzonitrile. The resulting mixture was heated and stirred for 24 hours. The pale yellow precipitate was filtered, washed with deionized water and ethyl ether, and dried under high vacuum to give a crude product. Recrystallization from tetrahydrofuran and acetone afforded the desired pure product (pale yellow solid; 15 mg).

$^1H$ NMR in acetone-$d_6$: δ: 7.75 (m, 2H), 7.25 (d, 1H), 7.13 (t, 1H), 4.01 (br, 3H), 3.96 (s, 3H). $^{195}Pt$ NMR δ-2241 ppm. Predicted HRMS for $C_8H_{10}Cl_2N_2OPtNa^+$: 437.971001 amu; found: 437.966919 amu.

X. Preparation of cis-amminecyclopentanecarbonitrildichloroeplatinum(II); $C_6H_{12}Cl_2N_2Pt$; $PtCl_2(NH_3L(C_5H_9CN)$ To a solution of $K[PtNH_3Cl_3]$ (150 mg) in 4 mL of deionized water was added 0.3 mL of cyclopentanecarbonitrile. The resulting mixture was heated and stirred for 24 hours. The pale yellow precipitate was filtered, washed with deionized water and ethyl ether, and dried under high vacuum to give a crude product. Recrystallization from tetrahydrfuran and acetone afforded a pure product (pale yellow solid; 20 mg).

$^1H$ NMR in Aceton-$d_6$: δ: 3.96 (br, 3H), 3.31 (m, 1H), 1.70 (m, 8H). $^{195}Pt$ NMR δ-2227 ppm. Predicted HRMS for $C_6H_{12}Cl_2N_2PtNa^+$: 399.991736 amu; found: 399.989054 amu.

XI. Preparation of cis-amminedichloro(2-methoxyphenylacetonitrile) platinum(II); $C_9H_{12}Cl_2N_2OPt$; $PtCl_2(NH_3)(2-CH_3OC_6H_4CH_2CN)$ To a solution of $K[PtNH_3Cl_3]$ (150 mg) in 6 mL of deionized water was added 2-methoxyphenylacetonitrile (208 mg). The resulting mixture was heated and stirred for 24 hours. The pale yellow precipitate was filtered, washed with deionized water and ethyl ether, and dried under high vacuum to give a crude product, which was recrystallized from tetrahydrofuran and acetone afforded the desired pure product (pale yellow solid, 10 mg).

$^1H$ NMR in acetone-$d_6$: δ: 7.30 (m, 2H), 7.00 (t, 1H), 6.92 (t, 1H), 3.83 (s, 3H), 3.71 (s, 2H). $^{195}Pt$ NMR δ-2250 ppm. HRMS calcd for $C_9H_{12}Cl_2N_2OPtNa^+$: 451.986651 amu; found: 451.987617 amu.

XII. Preparation of cis-amminedichloro(4-hydroxymethylbenzonitrile) platinum(II); $C_8H_{10}Cl_2N_2OPt$; $PtCl_2NH_3)(4-OHCH_2C_6H_4CN$ To a solution of $K[PtNH_3Cl_3]$ (150 mg) in 8 mL of deionized water was added 4-hydroxymethylbenzonitrile (200 mg). The resulting mixture was heated and stirred for 24 hours. The pale yellow precipitate was filtered, washed with deionized water and ethyl ether, and dried under high vacuum to give a crude product, which was recrystallized from tetrahydrofuran and acetone afforded the desired pure product (pale yellow solid, 30 mg).

$^1H$ NMR in acetone-$d_6$: δ: 7.84 (d, 2H), 7.61 (d, 2H), 4.73 (s, 2H), 4.02 (br, 3H). $^{195}Pt$ NMR δ-2254 ppm. Predicted HRMS for $C_8H_{10}Cl_2N_2OPtNa^+$: 437.971001 amu; found: 437.96984 amu.

XIII. Proposed Process for Preparation of cis-amminechloroidocyclohexanecarbonitrileplatinum(II)

To a solution of $K[PtNH_3Cl_3]$ (150 mg) in 4 mL of deionized water will be added sodium iodide (1.1 equivalent) at 0° C. The mixture will be stirred for approximately 15 minutes, and to the mixture will be added cyclohexanecarbonitrile (1.1 equivalent). The resulting mixture will then be stirred for approximately 2 hours. The pale yellow precipitate will be filtered, washed with deionized water followed by diethyl ether, and dried under high vacuum to obtain the crude product. Recrystallization from tetrahydrofuran and acetone will produce the purified product.

XIV. Proposed Process for Preparation of cis-amminediiodocyclohexanecarbonitrileplatinum(II)

To $PtCl_2(NH_3)(C_6H_{11}CN)$ (100 mg) in 5 mL of deionized water will be added 2 equivalents of silver sulfate. The reaction mixture will then be stirred for approximately 24 hours, and precipitate filtered. To the filtrate (3), a 1N hydrobromic acid aqueous solution (5 mL) will be added, and the resulting mixture stirred for approximately 2 hours. The precipitate will be filtered and washed with deionized water, followed by diethyl ether, to yield the desired yellow product.

XV. Proposed Process for Preparation of cis-amminediacetatocyclohexanecarbonitrileplatinum(II)

To $PtCl_2(NH_3)(C_6H_{11}CN)$ (100 mg) in 5 mL of deionized water will be added 2 equivalents of silver sulfate. The reaction mixture will be stirred for approximately 24 hours, and the precipitate filtered. To the filtrate (3), sodium acetate (2 equivalents) will be added, and the resulting mixture stirred for approximately 24 hours. The precipitate will then be filtered, and washed with deionized water followed by diethyl ether, to yield the desired yellow product.

XVI. Proposed Process for Preparation of diacetatodichloroamminecyclohexanecarbonitrileplatinum To $PtCl_2(NH_3)(C_6H_{11}CN)$ (100 mg) in 1.5 mL acetic acid will be added 9 equivalents of acetic anhydride in one aliquot. The reaction mixture will be stirred for several minutes, and to the mixture 1.5 equivalents of hydrogen peroxide solution (30%) will be added. The mixture will then be stirred for approximately one hour. The reaction will be quenched by slow addition of methanol. The precipitate will be filtered and washed with deionized water followed by diethyl ether, to yield the desired yellow product.

XVII. Proposed Process for Preparation of dichlorodihydroxyamminecyclohexanecarbonitrileplatinum(IV)

A mixture of the above complex from Example IV in 15% hydrochloric acid aqueous solution and methylene dichloride will be stirred for 45 minutes. The aqueous solution will then be separated and neutralized to pH 7.0. The precipitate will be filtered and washed with deionized water and diethyl ether, to produce the desired platinum (IV) compound as a yellow product.

XVIII. Proposed Process for Preparation of cyclohexanecarbonitrile trichloroplatinum (II)

To a solution of $(N(CH_3)_4)_2[PtCl_4]$ or $K_2[PtCl_4]$ in 5 mL of deionized water will be added the cyclohexanecarbonitrile (1 mmol). The reaction mixture will then be stirred for approximately 10 days. Solid will be filtered, and the filtrate evaporated to dryness. A small amount of acetone will be added to the residue, and solid filtered. The filtrate will then be evaporated to obtain the desired product.

XIX. Proposed Process for Preparation of cis-dichloromethylamminecyclohexanecarbonitrileplatinum(II)

To a solution of cyclohexanecarbonitrile trichloroplatinum (II) in deionized water will be added methylamine (2 equivalents) in methanol. The reaction mixture will then be stirred for approximately 24 hours at room temperature, and the yellow precipitate filtered, washed with water and acetone, and dried under high vacuum to yield the desired product.

XX. Proposed Process for Preparation of cis-ethylaminedichlorocyclohexanecarbonitrileplatinum(II)

To a solution of cyclohexanecarbonitrile trichloroplatinum(II) in deionized water wil be added ethylamine (2 equivalents) in methanol. The reaction mixture will then be stirred for approximately 24 hours at room temperature, and the yellow precipitate filtered, washed with water and acetone, and dried under high vacuum to yield the desired product.

Specific Examples of In Vitro Experimental Results

Experiments were performed to compare cytotoxicity against a cancer cell line (A27880/WT) of two of the complexes described above against cisplatin. These complexes (and cisplatin also) had Formulas α and β as follows:

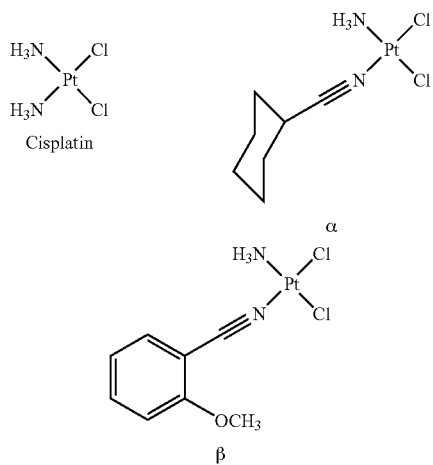

In these experiments, the cells were incubated with different concentrations of each of the agents for one hour and for two hours, and cell survival was determined by SRB (Sulfo Rhodamine B) assay. Table 1 show the results of these experiments, where "$EC_{50}$" denotes Effective Concentration (i.e., $IC_{50}$). It can be ascertained from these number that the $EC_{50}$ is lower for the novel mononitrile-containing platinum complexes disclosed in the present invention than for cisplatin, thus indicating that they are more potent and effective as cytotoxic agents.

TABLE 1

| Platinum Complex | $EC_{50}$ | |
|---|---|---|
| | 1 hour | 2 hours |
| Cisplatin | 10.84 | 4.27 |
| Analog α | 5.61 | 4.30 |
| Analog β | 4.13 | 2.89 |

Dosage and Administration

The experimental results above provide a basis on which to extrapolate to determine the appropriate therapeutic dosage. Routine animal experimentation would also serve as a basis for extrapolation (i.e., typically based on a weight-to-weight comparison of human subjects and animals), to clarify the parameters of the dose range. Human clinical studies could further clarify optimal dosing through a conventional dose ranging study, or a single dose trial based on an extrapolated preferred dose.

The compounds described herein may be administered by any suitable method permitting systemic availability, including but not limited to intravenous, parenteral, and oral administration. Appropriate formulations and excipients are well-known, would be expected to be the same or similar to those used for cisplatin administration, and are set forth further in standard references, including *Remington's Pharmaceutical Sciences*, 18th Edition, Mack Publishing Company, Easton, Pa., (2004).

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A platinum complex having the following substituent groups bonded thereto:
    (i) a nitrile-containing group;
    (ii) a carrier ligand which is selected from a group consisting of: a primary, secondary or tertiary amine, or pyridine, pyrrole, pyrazole, or imidazole, and which is capable of forming a hydrogen bond with a base in a DNA or RNA; and
    (iii) at least one leaving group which can be displaced by water or by hydroxide ions to form an active species; wherein said platinum complex is not cis[Pt(EtCN)(NH$_3$)(Cl$_2$)].

2. The complex of claim 1, wherein the leaving groups can be replaced by aquated species in vivo, whereby the resulting complex can form complexes with DNA or RNA at the Guanine or Adenine bases thereof.

3. The complex of claim 1, wherein there is one leaving group which is selected from the group consisting of: carboxylate, alkoxyl, peroxide, sulfur, disulfide, sulfoxide, chloride, bromide, fluoride, iodide, amine, pyridine, pyrrole, chlorate, nitrate, nitrite, sulfate, sulfite, phosphate, carbonyl, phosphite, phosphide, or phosphine.

4. The complex of claim 1, wherein there are two leaving groups which are the same or different, and each leaving group is one species selected from the group consisting of: carboxylate, alkoxyl, peroxide, sulfur, disulfide, sulfoxide, chloride, bromide, fluoride, iodide, amine, pyridine, pyrrole, chlorate, nitrate, nitrite, sulfate, sulfite, phosphate, phosphite, phosphide, phosphine, thio phosphonate, alkyl phosphoramidates, or phosphoramidate.

5. The complex of claim 4, wherein the active species are the same or different, and are hydroxyl, aquo or OH$_2{}^+$/OH.

6. The complex of claim 1, wherein the nitrile containing group is not so large as to interfere with chelation of the complex with DNA.

7. The complex of claims 1 or 6, wherein the carrier ligands are charge neutral in the complex and not so large as to interfere with chelation of the complex with DNA.

8. The complex of claim 1, wherein the carrier ligand is represented as RN, and R is selected from the group consisting of: alkyl, cycloalkyl, or aryl groups;
and said platinum complex is not cis[Pt(EtCN)(NH$_3$)(Cl$_2$)]

9. The complex of claim 6, wherein the nitrile containing group is selected from the group consisting of: alkyl, cycloalkyl, aromatic and acetate groups.

10. The compound of claim 1, wherein the carrier ligand is capable of forming a hydrogen bond with a base in a DNA or RNA.

11. The compound of claim 1, wherein, following displacement of the leaving group, the resulting compound can form complexes with DNA or RNA at the Guanine or Adenine bases thereof.

12. The compound of claim 11, wherein the resulting compound can cross-link complementary strands at the purine bases, thereof.

13. A platinum complex having the following structural formula:

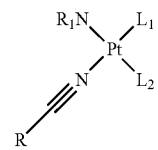

wherein,
    (i) L$_1$ or L$_2$, or both L$_1$ and L$_2$, are leaving groups capable of being displaced by water or by hydroxide ions to form an active species;
    (ii) R$_1$N is selected from a group consisting of: a primary, secondary or tertiary amine, pyridine, pyrrole, pyrazole, or imidazole; and wherein R$_1$ is selected from the group consisting of: hydrogen, alkyl, cycloalkyl, or aromatic; and (iii) R is selected from a group consisting of: alkyl, alkyl, cycloalkyl, aryl or acetate, or another functional group not so large as to cause spatial or steric interference with chelation of the complex with DNA;
and wherein said platinum complex is not cis[Pt(EtCN)(NH$_3$)(Cl$_2$)].

14. The compound of claim 13, wherein R$_1$ is H$_3$ and R is hex-cycloalkyl or aryl methoxy.

15. The compound of claim 13, wherein R$_1$ is H$_3$ and R is methoxybenzo.

16. The compound of claim 13, wherein R$_1$ is H$_3$ and R is methoxy-propio.

17. The compound of claim 13, wherein R$_1$ is H$_3$ and R is ethoxybenzo.

18. The compound of claim 13, wherein R$_1$ is H$_3$ and R is cyclopropylcyano.

19. The compound of claim 13, wherein R$_1$ is H$_3$ and R is furo.

20. The compound of claim 13, wherein R$_1$ is H$_3$ and R is 2-methoxy-benzo.

21. The compound of claim 13, wherein R$_1$ is H$_3$ and R is cyclopentane.

22. The compound of claim 13, wherein R$_1$ is H$_3$ and R is methoxy-phenyl.

23. The compound of claim 13, wherein R$_1$ is H$_3$ and R is hydroxy-methyl benzene.

24. The compound of claim 13 wherein R$_1$ is H$_3$ and R is cyclopentanecarbo.

25. The compound of claim 13, wherein R$_1$ is H$_3$ and R is cyclohexane carbo.

26. The compound of claim 13, wherein R$_1$ is H$_3$ and R is 2-methoxyphenylaceto.

27. The compound of claim 13, wherein R$_1$ is H$_3$ and R is 4-hydroxymethylbenzo.

28. The compound cyclohexanecarbonitrile trichloroplatinum.

29. The compound cis-dichloromethylamminecyclohexanecarbonitrileplatinum.

30. The compound cis-ethylamminedichlorocyclohexanecarbonitrileplatinum.

31. A compound having the following formula:

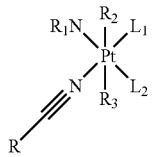

wherein;
L$_1$ or L$_2$, or both L$_1$ and L$_2$, are capable of being displaced by water, hydroxide ions or other nucleophiles;
R$_1$N is selected from a group consisting of: a primary, secondary, tertiary amine, pyridine, pyrrole, pyrazole, imidazole and R$_1$ is alkyl, cycloalkyl, or aryl; and
R$_2$ and R$_3$ are the same or different groups and are selected from the group consisting of: F, C, Cl, Br, I, N, S, or OR$_6$ (wherein OR$_6$ is carboxylate, alkoxyl, hydroxyl, or water).

32. A compound having the following formula:

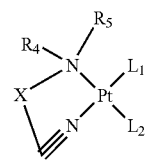

wherein;
L$_1$ or L$_2$, or both L$_1$ and L$_2$, are capable of being displaced by water, hydroxide ions or other nucleophiles;
R$_1$N is selected from a group consisting of: a primary, secondary, tertiary amine, pyridine, pyrrole, pyrazole, imidazole;
R$_1$, R$_4$ and R$_5$, are the same or different, and are is selected from a group consisting of: alkyl, cycloalkyl, or aryl; and
X is an alkyl group or alkyl chain of between 1 and 20 atoms, which can be saturated or unsaturated.

33. The compound of claim 32, wherein the alkyl chain of between 1 and 20 atoms includes one or more of nitrogen, sulfur, and oxygen.

34. The compound of any one of claims 13, 31, or 32, wherein the L$_1$ or L$_2$ are the same or different, and are selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates.

35. The compound of any of claims 13, 31, or 32, wherein the active species is hydroxyl, aquo or is OH$_2$$^+$/OH.

36. A compound comprising platinum, having:
(i) a nitrile-containing group bonded thereto;
(ii) one Guanine or Adenine base of a nucleotide hydrogen bonded thereto;
(iii) a hydroxyl group, aquo group, or OH$_2$$^+$/OH, or a leaving group which is selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramodates, bonded thereto; and
(iv) a carrier ligand which is selected from the group consisting of: a primary, secondary or tertiary amine, or pyridine, pyrrole, pyrazole, or imidazole, bonded thereto.

37. A compound comprising platinum, having:
(i) a nitrile-containing group bonded thereto;
(ii) two Guanine or Adenine bases of a nucleotide or an oligonucleotide hydrogen, bonded thereto; and
(iii) a carrier ligand which is selected from the group consisting of: a primary, secondary or tertiary amine, or pyridine, pyrrole, pyrazole, or imidazole, bonded thereto.

38. A compound comprising the structure:

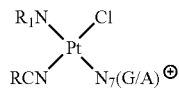

wherein;
(i) Cl is selected from the group consisting of: carboxylate, alkoxyl, hydroxyl, water, aquo, an $OH_2^+/OH$ group, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates;
N7(G/A) denotes a bond to the 7 position of a Guanine or Adenine base of a nucleotide or an oligonucleotide;
(ii) $R_1N$ is a primary, secondary or tertiary amine, or pyridine, and R1is selected from the group consisting of: alkyl, cycloalkyl, or aromatic; and
RCN is a nitrile, wherein R is alkyl, cycloalkyl, aryl or acetate.

39. A compound having the structure of 13 or 14 below:

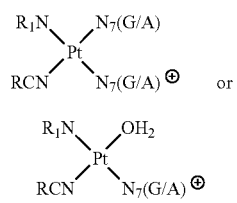

wherein;
(i) N7(G/A) denotes a bond to the 7 position of a Guanine or Adenine base of a nucleotide or an oligonucleotide;
(ii) $R_1N$ is a primary, secondary or tertiary amine, or pyridine, and wherein R1 is selected from the group consisting of: alkyl, cycloalkyl, or aromatic, acetate; and
RCN is a nitrile, and wherein R is alkyl, cycloalkyl, aryl or acetate.

40. A process of making a compound having the structure

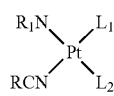

wherein
(i) RCN is a nitrile, and wherein R is selected from the group consisting of: alkyl, cycloalkyl, aryl or acetate; $R_1$ is hydrogen, alkyl, cycloalkyl, aryl or acetate; and $L_1$ and $L_2$ are the same or different, and are selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates;
(ii) $R_1N$ is a primary, secondary or tertiary amine, or pyridine, and R1 is selected from the group consisting of: alkyl, cycloalkyl, or aromatic; and comprising:
(a) reacting $Et_4N[R_1NPtCl_3]$ or $K[R_1NPtCl_3]$, with an RCN nitrile, wherein R is alkyl, cycloalkyl, aryl or acetate, and $R_1$ is hydrogen, alkyl, cycloalkyl, or aryl,
(b) reacting the product of step (a) with $AgNO_3$ or $Ag_2SO_4$; and
(c) reacting the product of step (b) with $L_1$ and $L_2$, wherein $L_1$ and $L_2$ are the same or different, and are selected from the group consisting of: carboxylate, alkoxyl, hydroxy water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates.

41. The process of claim 40, wherein step (a) includes NaI in the reaction mixture.

42. The process of claim 40 or claim 41, further including the step of reacting the product of step (c) with $R_2$ and $R_3$, wherein $R_2$ and $R_3$ are the same or different, and are selected from the group consisting of: F, Cl, Br, I, N, S, or $OR_6$ (wherein, $OR_6$ is carboxylate, alkoxyl, hydroxyl, or water).

43. The process of claim 40 or claim 41, wherein $L_1$ and $L_2$ are chloride, $R_1$ is hydrogen and R is benzene.

44. The process of claim 40 or claim 41, wherein $L_1$ and $L_2$ are chloride, $R_1$ is hydrogen and R is methoxybenzo.

45. The process of claim 40 or claim 41, wherein $L_1$ and $L_2$ are chloride, $R_1$ is hydrogen and R is methoxy-propio.

46. The process of claim 40 or claim 41, wherein $L_1$ and $L_2$ are chloride, $R_1$ is hydrogen and R is ethoxybenzo.

47. The process of claim 40 or claim 41, wherein $L_1$ and $L_2$ are chloride, $R_1$ is hydrogen and R is cyclohexane.

48. The process of claim 40 or claim 41, wherein $L_1$ and $L_2$ are chloride, $R_1$ is hydrogen and R is cyclopropylcyano.

49. The process of claim 40 or claim 41, wherein $L_1$ and $L_2$ are chloride, $R_1$ is hydrogen and R is furo.

50. The process of claim 40 or claim 41, wherein $L_1$ and $L_2$ are chloride, $R_1$ is hydrogen and R is 2-methoxy-benzo.

51. The process of claim 40 or claim 41, wherein $L_1$ and $L_2$ are chloride, $R_1$ is hydrogen and R is cyclopentanecarbo.

52. The process of claim 40 or claim 41, wherein $L_1$ and $L_2$ are chloride, $R_1$ is hydrogen and R is 2-methoxyphenylaceto.

53. The process of claim 40 or claim 41, wherein $L_1$ and $L_2$ are chloride, $R_1$ is hydrogen and R is 4-hydroxymethylbenzo.

54. A process of making a compound having the structure:

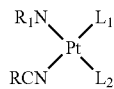

wherein;
(i) RCN is a nitrile and R is alkyl, cycloalkyl, aryl or acetate; $R_1$ is hydrogen, alkyl, cycloalkyl, aryl or acetate; and $L_1$ and $L_2$ are the same or different, and are selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates;

(ii) $R_1N$ is a primary, secondary or tertiary amine, or pyridine, and R1 is alkyl, cycloalkyl, aromatic, or acetate; and comprising:

(a) reacting $(Me_4N)_2[Pt(L_1$ and/or $L_2)_4]$ or $K_2[Pt(L_1$ and/or $L_2)_4]$ with a nitrile RCN, wherein R is alkyl, cycloalkyl, aryl, or acetate; and $L_1$ and $L_2$, are the same or different, and are selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates and phosphoramidates; and (b) reacting the product of step (a) with $R_1N$, wherein is $R_1$ is hydrogen, alkyl, cycloalkyl, aryl or acetate;

wherein said platinum complex is not $cis[Pt(EtCN)(NH_3)(Cl_2)]$.

55. A platinum complex comprising:
(i) one nitrile functional group covalently bonded to the platinum;
(ii) at least one nitrogen containing ligand; and
(iii) at least one leaving group which can be substituted with a hydroxyl or another nucleophilic group; and
wherein, said platinum complex, in a Sulfo rhodamine B cytotoxicity assay against cancer cell line A27880/WT, can provide an $EC_{50}$ less than that of cisplatin in the same assay and assay conditions.

56. The platinum complex of claim 55, wherein the $EC_{50}$ is 7.5 µM or less following one hour of exposure to said platinum complex.

57. The platinum complex of claim 55, wherein the $EC_{50}$ is 5 µM or less following two hours of exposure to said platinum complex.

58. The platinum complex of claim 55, wherein the nitrogen containing ligand is capable of forming hydrogen bonds with the bases in DNA or RNA.

59. The platinum complex of claim 55, wherein the leaving group can cross-link purines in complementary strands of DNA or RNA.

60. The platinum complex of claim 55, wherein the nitrogen containing ligand is selected from the group consisting of: a primary, secondary or tertiary amine, or pyridine, pyrrole, pyrazole, or imidazole, where the nitrogen can be represented as RN;

wherein R is hydrogen, alkyl, cycloalkyl, or aryl.

61. The platinum complex of claim 55, wherein the leaving group is selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates or phosphoramidates.

62. The platinum complex of claim 55, wherein there are two leaving groups, which are the same or different, and each is one selected from the group consisting of: carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates or phosphoramidates.

63. The platinum complex of claim 55, wherein following substitution, an active species is formed, which is the same or different, and is hydroxyl, aquo or $OH_2^+/OH$.

64. A platinum complex having the structure α:

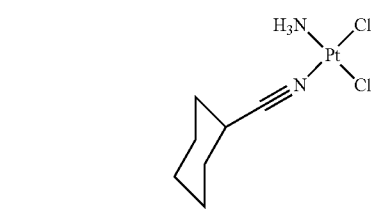

65. A platinum complex having the structure β:

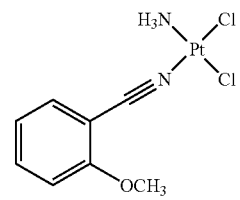

* * * * *